(12) United States Patent
Muraoka et al.

(10) Patent No.: US 6,334,358 B2
(45) Date of Patent: Jan. 1, 2002

(54) FRICTION TEST APPARATUS

(75) Inventors: Kiyoshige Muraoka; Jun Nishibayashi, both of Kobe; Chikahiro Sato, Kunitachi, all of (JP)

(73) Assignees: Sumitomo Rubber Industries, Ltd., Kobe; Japan Applied Technology Inc., Tokyo, both of (JP)

( * ) Notice: Subject to any disclaimer, the term of this patent is extended or adjusted under 35 U.S.C. 154(b) by 0 days.

(21) Appl. No.: 09/729,691

(22) Filed: Dec. 6, 2000

(30) Foreign Application Priority Data

Dec. 16, 1999 (JP) .......................... 11-356915

(51) Int. Cl.[7] .............................. G01M 17/02
(52) U.S. Cl. .............................. 73/146; 73/9
(58) Field of Search .................... 73/8, 9, 146

(56) References Cited

U.S. PATENT DOCUMENTS 4,458,527 A * 7/1984 McFarland et al. .............. 73/9

FOREIGN PATENT DOCUMENTS

| JP | 0215846 | * | 9/1987 | ............... 73/9 |
| JP | B2-3-10062 | | 2/1991 | |
| JP | B2-3-63012 | | 9/1991 | |
| JP | U-5-66545 | | 9/1993 | |
| JP | A-6-221990 | | 12/1994 | |

* cited by examiner

Primary Examiner—Robert Raevis
(74) Attorney, Agent, or Firm—Birch, Stewart, Kolasch & Birch, LLP (57) ABSTRACT

A friction test apparatus with rotating friction means and endless belt set around one pair of rotating drums, has a meandering prevention mechanism to prevent the belt from meandering; and a belt supporting means which has a flat stage facing the inner face of the belt and a water-supplying mechanism which supplies water between the flat stage and the belt from an upstream side of belt rotation direction to the flat stage. Said apparatus also has a sample holder driving means which has a three-component detecting portion which detects loads on the sample in front-rear direction, left-right direction and upper-lower direction, and the sample holder driving means is having a slip angle regulation mechanism for regulation of a slip angle of the sample attached to the sample holder to the belt, and constructed so as to adjust the slip ratio of the sample attached to the sample holder to the belt.

4 Claims, 8 Drawing Sheets

FRICTION TEST APPARATUS

BACKGROUND OF THE INVENTION

1. Field of the Invention

This invention relates to a friction test apparatus for viscoelastic materials such as rubber, etc. To describe further in detail, this invention relates to a friction test apparatus with which similar effects to that of friction test of prototype tires are obtained by conducting friction test with a sample of composition material of the tire and without making various prototype tires.

2. Description of the Related Art

Conventionally, as a friction test apparatus for viscoelastic materials for tires, a friction test apparatus of slide resistance type in which friction test is conducted by sliding a sample composed of a viscoelastic material on a friction face, and a friction test apparatus of rotating disc type as disclosed by Japanese Patent Publication Number 3-10062 are in the mainstream. And, a friction test apparatus of rotation type on the road as disclosed by Japanese Patent Publication Number 3-63012 is also proposed.

Further, as friction test apparatuses of recent types, an apparatus in which a sample is made contact an inner face of a cylindrical rotating drum to conduct friction test, an apparatus of slide resistance type in which friction characteristics on an actual road are measured as disclosed by Japanese Utility Model Provisional Publication Number 5-66545, and an improved type of the cylindrical rotating drum as disclosed by Japanese Patent Provisional Publication Number 6-221990 are also proposed.

However, in these conventional apparatuses as described above, following problems occurs.

① In friction test apparatuses of slide resistance type, slide resistance is mainly measured because the resistance is measured with the sample sliding on the friction face. Although rolling resistance should be measured in friction test of a tire, friction data of the friction test with slide resistance are used, and the test condition is different from actual service condition.

② In the apparatuses in which the sample is made contact and rotated on the inner face or the outer face of the rotating drum, curved faces of the rotating drum and the sample contact each other, load distribution on the sample is different from that in actual service conditions of a tire when the load is increased, and reliability of the test becomes low thereby.

③ In the apparatus in which the sample is made contact and rotated on a rotating flat board to conduct friction test, centrifugal force always works on the sample outward, and difference of rotation speed on an inner side and an outer side of the flat board generates difference in rotation speed against the flat board on an inner part and an outer part of the sample. Measured value of the friction considerably varies depending on interpretation of the difference in the rotation speed.

④ To solve the problems of ② and ③, it is feasible to make the rotation body (the rotating drum or the flat board) larger than the sample. Although the measurement is improved to some degrees with this modification, it is insufficient to obtain accurate test results. And, this modification causes a problem that the apparatus itself becomes large.

It is therefore an object of the present invention, solving the problems above, to provide a friction test apparatus in which friction test of a viscoelastic material is easily and accurately conducted by simulating friction test with a sample of product and without making prototypes of actual product.

BRIEF DESCRIPTION OF THE DRAWINGS

The present invention will be described with reference to the accompanying drawings, in which.

DESCRIPTION OF THE PREFERRED EMBODIMENTS

Preferred embodiments of the present invention will now be described with reference to the accompanying drawings.

Figure 1:
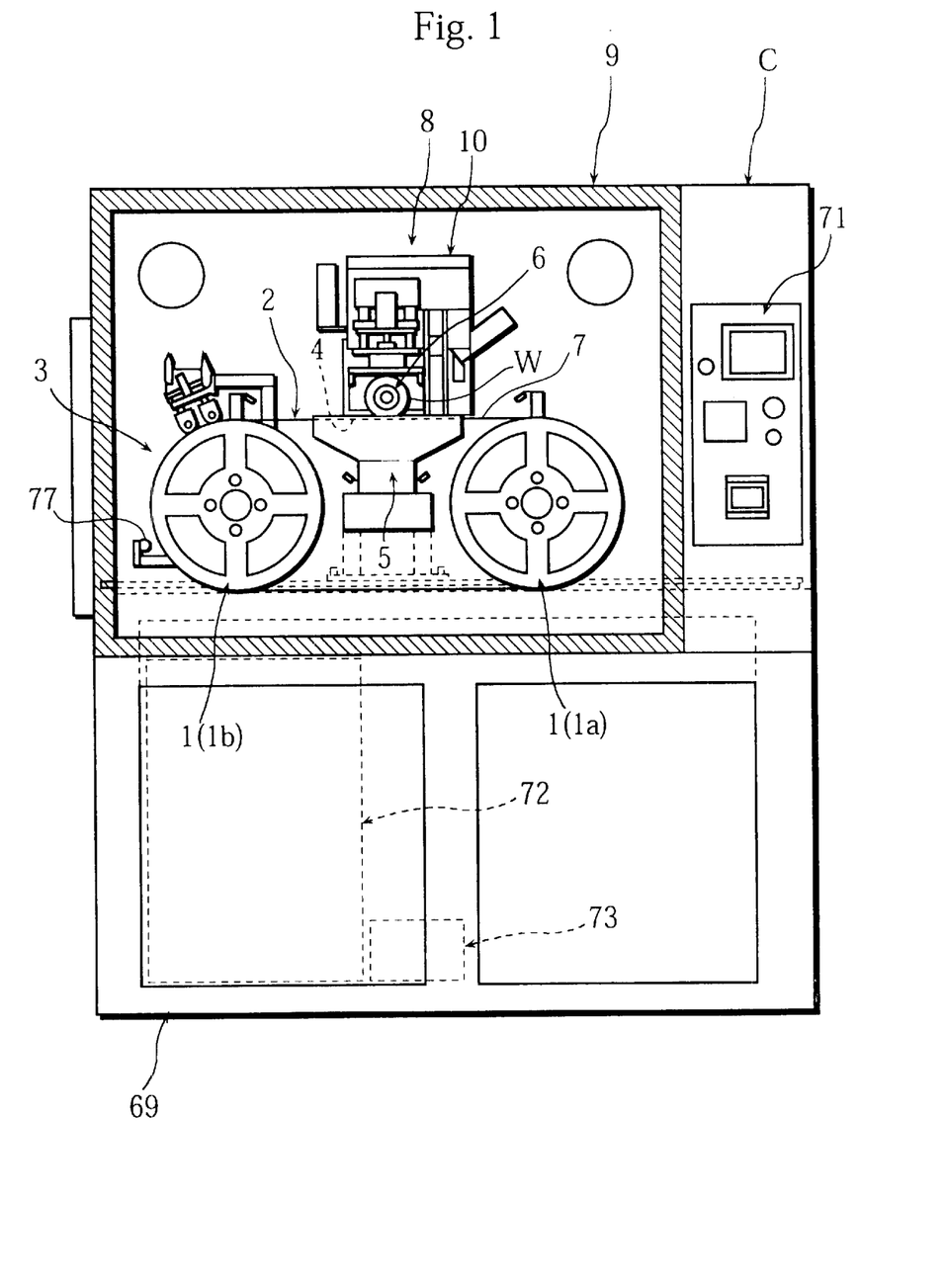
FIG. 1 is a front view with a partial cross-section showing an embodiment of the friction test apparatus of the present invention.

FIG. 1 shows an embodiment of a friction test apparatus relating to the present invention. This friction test apparatus is provided with a rotating friction means 3 having an endless belt 2 set around one pair of rotating drums 1, a belt supporting means 5 disposed near an inner face 4 of the belt 2, a sample holder 6 to which a sample W is detachably attached, and a sample holder driving means 8 by which the sample W attached to the sample holder 6 is pressed to and part from an outer face 7 of the belt 2. The pair of rotating drums 1, the endless belt 2, and the sample holder 6 of the rotating friction means 3 are enclosed in a constant temperature chamber 9 of which temperature can be adjusted. And, C represents a casing and 71 represents an operation unit.

To describe concretely, as shown in FIG. 1 through FIG. 4, the sample holder driving means 8 is provided with a sample measuring portion 10 which holds the sample holder 6 as to rotate around a horizontal axis $P_1$ and oscillate around a vertical axis $P_2$, a slip angle regulation mechanism 11 which oscillates the sample measuring portion 10 around the vertical axis $P_2$, and a back-and-forth transfering mechanism 12 which moves the slip angle regulation mechanism 11 and the sample measuring portion 10 in back-and-forth direction, namely, a direction at right angles with the belt 2.

Figure 2:
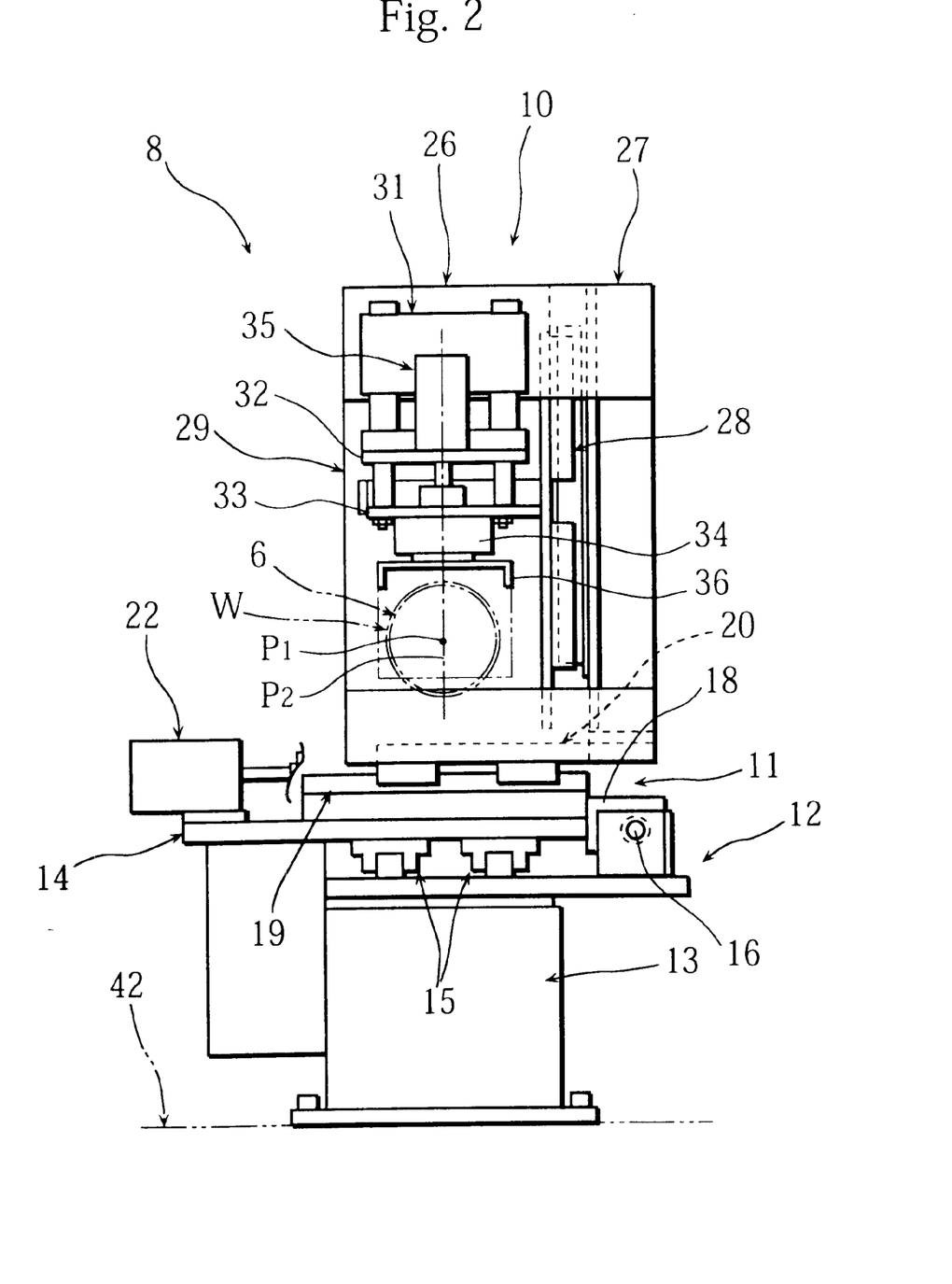
FIG. 2 is a front view of a principal portion showing a sample holder driving means.
Figure 3:
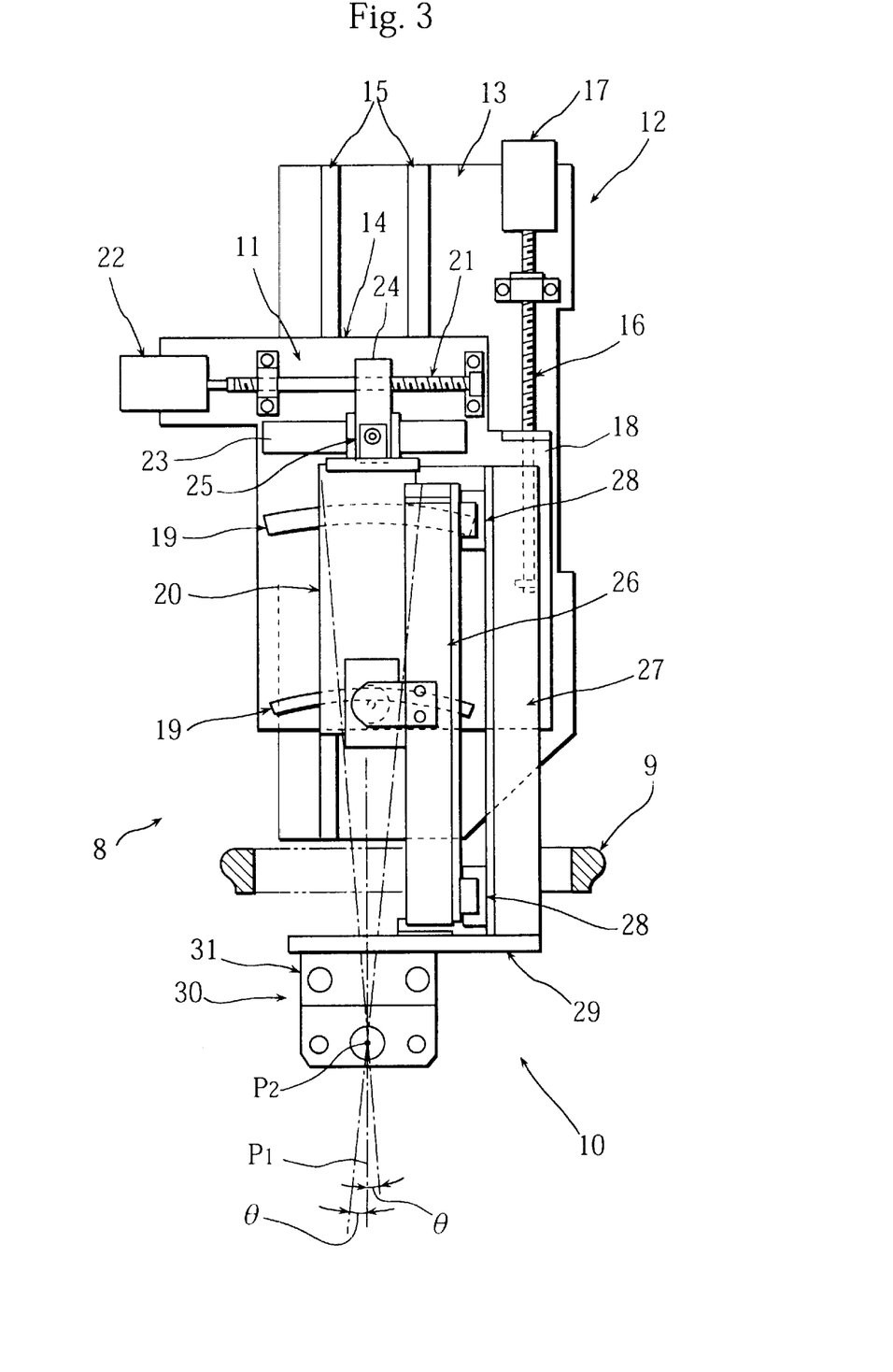
FIG. 3 is a top view of a principal portion showing a sample holder driving means.

The back-and-forth transfering mechanism 12 is provided with a stage portion 13 fixed to a frame plate 42 in the casing C on a back side of the constant temperature chamber 9, a back-and-forth moving plate 14 disposed on an upper face side of the stage portion 13, a pair of linear guides 15 disposed in the back-and-forth direction between the stage portion 13 and the back-and-forth moving plate 14, a screw shaft 16 in the back-and-forth direction disposed on the upper face of the stage portion 13 as to freely rotate, a motor 17 fixed to the upper face of the stage portion 13 to drive the screw shaft 16 to rotate, and a nut portion 18 fixed to the back-and-forth moving plate 14 and screwed to the screw shaft 16. That is to say, the back-and-forth transfering mechanism 12 is constructed as to move the back-and-forth moving plate 14 unitedly formed with the nut portion 18 in the back-and-forth direction by rotating the screw shaft 16 in a direction and the other.

And, the slip angle regulation mechanism 11 is provided with a pair of curved guides 19, one of which is disposed on a front side and the other is on a rear side, formed with a predetermined radius of curvature of which center is the vertical axis $P_2$ and disposed on the back-and-forth moving plate 14 of the back-and-forth transfering mechanism 12, an oscillating plate portion 20 disposed on the pair of curved guides 19 as to freely slide, a screw shaft 21 in longitudinal direction at right angles with the back-and-forth direction disposed on the back-and-forth moving plate 14 as to freely rotate, a motor 22 fixed to the back-and-forth moving plate 14 to drive the screw shaft 21 to rotate, a guiding portion 23 disposed on the back-and-forth moving plate 14 to be parallel to the screw shaft 21, a nut portion 24 screwed to the screw shaft 21 and freely slid along the guiding portion 23, and a connecting portion 25 which connects the oscillating plate portion 20 to the nut portion 24 as to oscillate around the vertical axis $P_2$. That is to say, the slip angle regulation mechanism 11 is constructed as to oscillate the oscillating plate portion 20 left and right by rotating the screw shaft 21 in a direction and the other. In this case, the vertical axis $P_2$ is at the right angles with the rotating axis $P_1$ of the sample holder 6 and going through a contact point of the sample W attached to the sample holder 6 and the endless belt 2 (refer to FIG. 6 and FIG. 9).

And, the sample measuring portion 10 is provided with a fixation portion 26 disposed on the oscillating plate portion 20 of the slip angle regulation mechanism 11, a sliding portion 27 disposed on a right side face of the fixation portion 26 through one pair of linear guides 28 of vertical direction as to freely slide in the vertical direction, an attachment plate 29 fixed to a front end of the sliding portion 27, and a sample holder attachment portion 30 disposed on a front face side of the attachment plate 29 and holding the sample holder 6 as to rotate around the horizontal axis $P_1$ and oscillate around the vertical axis $P_2$.

Figure 4:
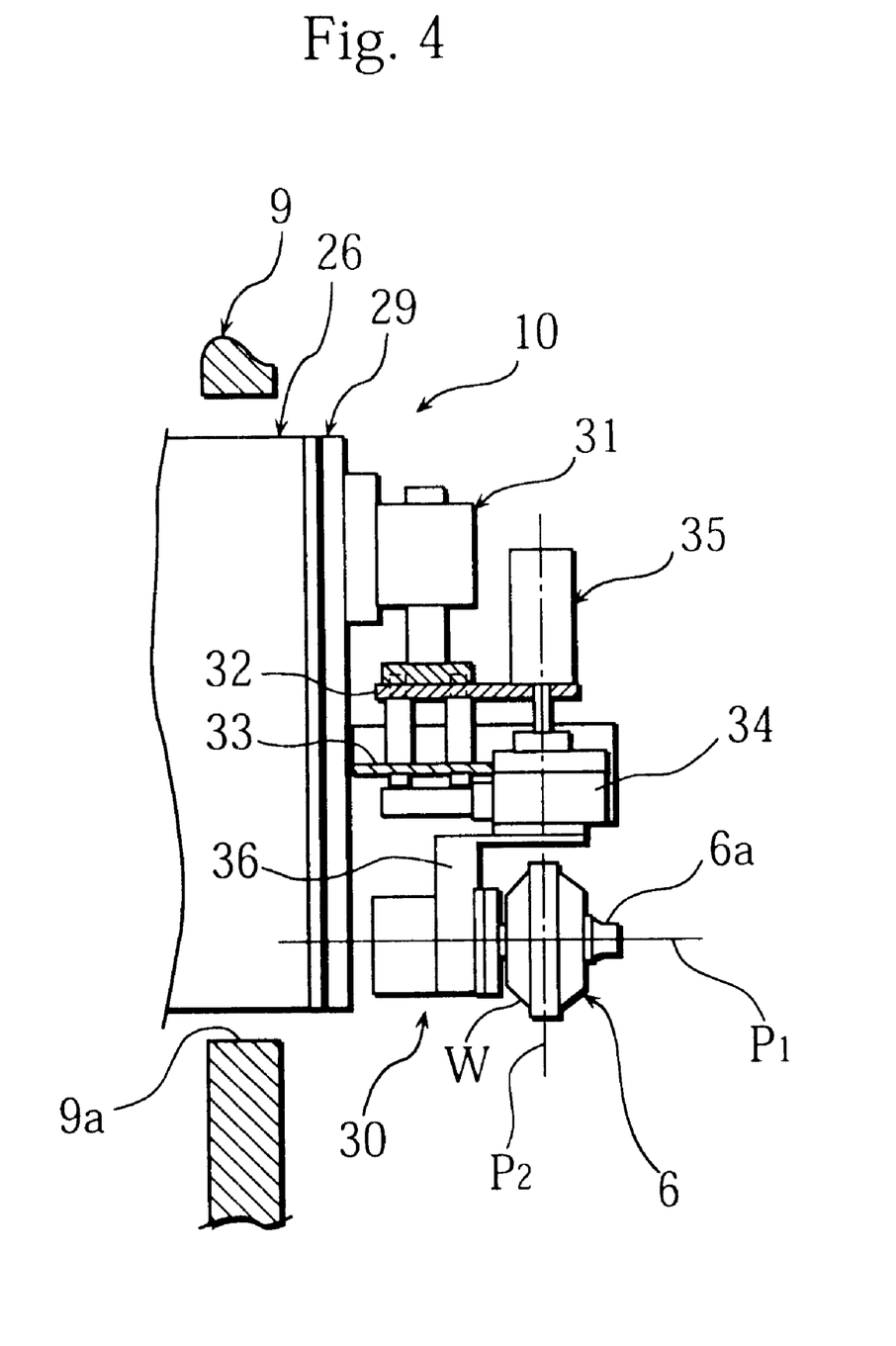
FIG. 4 is a cross-sectional side view of a principal portion showing a sample holder and a sample held by a sample measuring portion of the sample holder driving means.

The sample holder attachment portion 30, inserted into the constant temperature chamber 9 through a hole portion 9a on a rear wall of the constant temperature chamber 9, is provided with a sample transfer cylinder 31 attached to a front face of the attachment plate 29, an upper attachment plate 32 disposed on a lower end of the sample transfer cylinder 31, a lower attachment plate 33 disposed below the upper attachment plate 32 through plural cylindrical posts, a three-component detecting portion 34 attached to the lower attachment plate 33 and on the vertical axis $P_2$, a sample loading cylinder 35 of which main body is fixed to the upper attachment plate 32 and an end of a rod is fixed to an upper end of the three-component detecting portion 34, and a holding body 36 disposed on a lower end of the three-component detecting portion 34 to hold the sample holder 6 as to freely rotate around the horizontal axis $P_1$.

Therefore, the sample holder driving means 8 is constructed as transmit torque from a motor (not shown in Figures) enclosed in the sliding portion 27 to the sample holder 6 through a rotational force transmitting mechanism. Further, rotation speed of the sample holder 6 is adjustable to adjust slip ratio of the sample W attached to the sample holder 6 to the endless belt 2. And, the sliding portion 27 encloses a (later described) torque detecting portion, a load control portion, an air-pressure source unit, etc.

Figure 5:
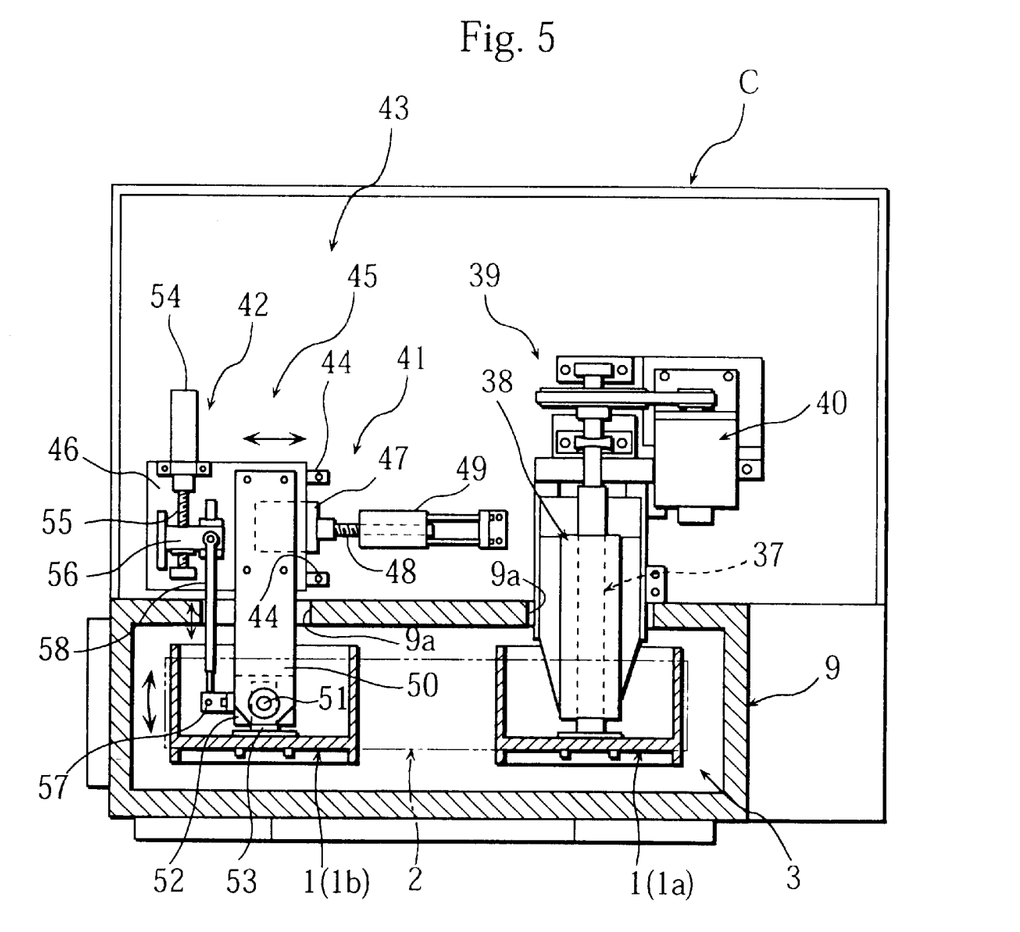
FIG. 5 is a cross-sectional top view of a principal portion showing a rotating friction means.

Next, as shown in FIG. 1 and FIG. 5, in the rotating friction means 3, one of the pair of rotating drums is a driving drum, and the other is a driven drum. A rotation driving shaft 37 of the driving rotating drum 1 (1a) is held by a bearing holder 38 fixed to a frame plate 43 as to freely rotate, protruding to a back face side through the hole portion 9a of the constant temperature chamber 9, and connected to a motor 40 through a rotational force transmitting mechanism 39 composed of pulleys and belts.

And, on the driven rotating drum 1(1b) side, a drum transfering mechanism 41 which attaches and detaches the belt 2 and adjusts tension by closing and parting the driven rotating drum 1b to and from the driving rotating drum 1a and a meandering prevention mechanism 45 to prevent the belt 2 from meandering are disposed. And, 77 represents an air blowing portion.

The drum transfering mechanism 41 is provided with one pair of guide rails 44 disposed on the frame plate 43 in horizontal direction, a sliding plate 46 disposed on the pair of guide rails 44 as to freely slide in the horizontal direction, a motor 47 fixed to a lower face of the sliding plate 46, a screw shaft 48 unitedly formed with a shaft of the motor 47, a nut portion 49 fixed to the frame plate 43 and screwing to the screw shaft 48, a holding rod 50 of which rear end is fixed to an upper face of the sliding plate 46 and front end is inserted to the constant temperature chamber 9 through the hole portion 9a of the constant temperature chamber 9, an oscillation body 52 attached to the front end of the holding rod 50 with a vertical shaft 51 as to oscillate, and a short shaft 53 of which rear end side is attached to the oscillation body 52 as to freely rotate and front end is fixed to the rotating drum 1(1b). That is to say, the drum transfering mechanism 41 is constructed as to close and part the the driven rotating drum 1b to and from the driving rotating drum 1a through the sliding plate 46 and the holding rod 50 by rotating the screw shaft 48 in a direction and the other with the motor 47.

Figure 6:
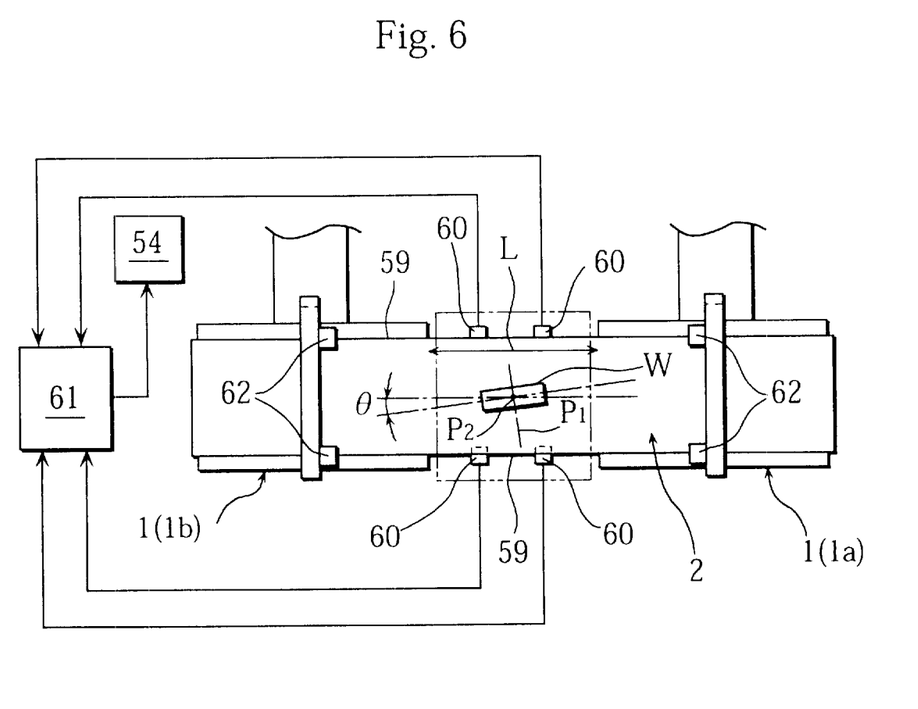
FIG. 6 is an explanatory view showing a sensor and a control portion of a meandering prevention mechanism.
Figure 7:
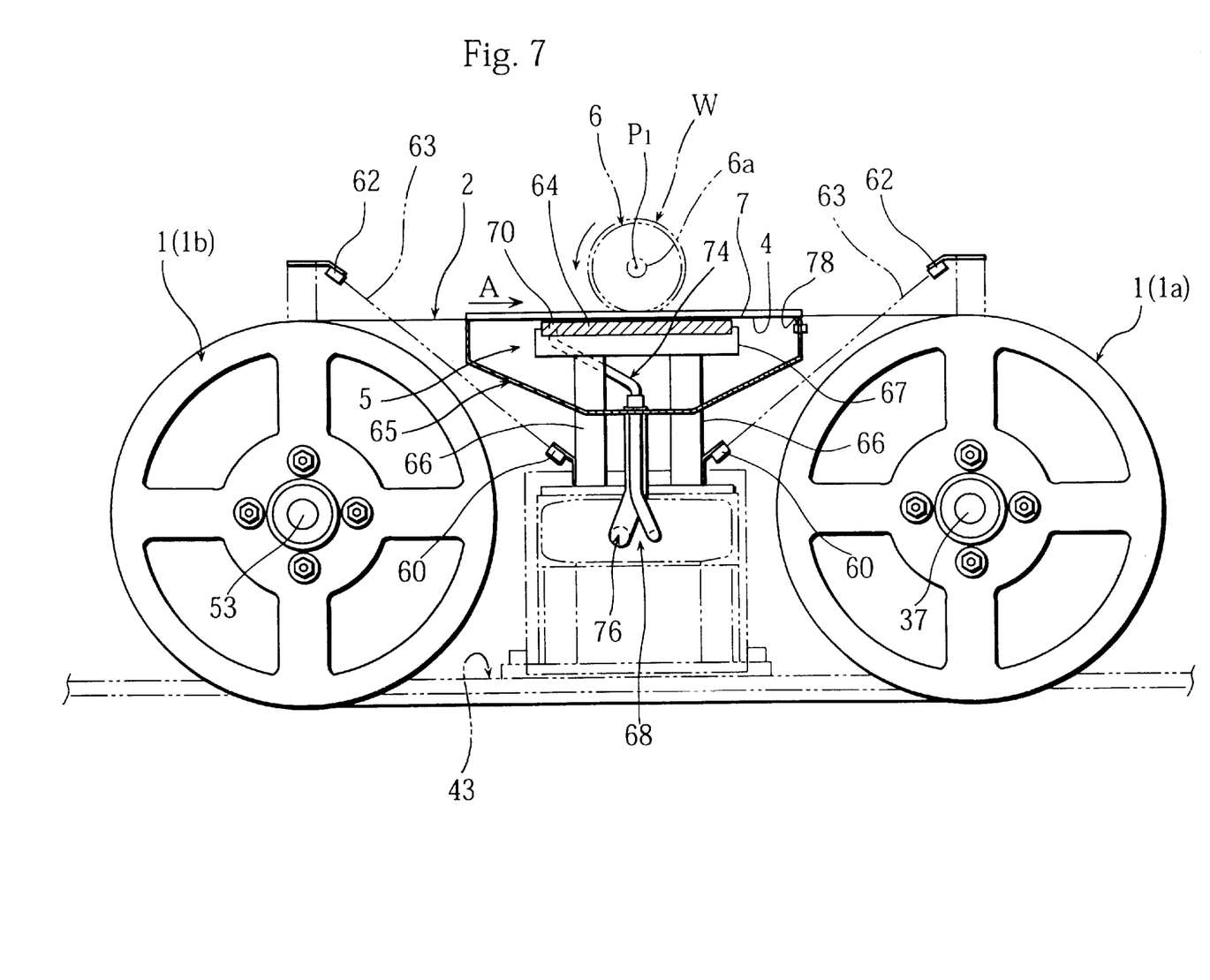
FIG. 7 is a cross-sectional front view of a principal portion showing a supporting means.

On the other hand, the meandering prevention mechanism 45 is, as shown in FIG. 5 through FIG. 7, provided with a motor 54 fixed to the sliding plate 46, a screw shaft 55 in the back-and-forth direction unitedly formed with a shaft of the motor 54, a nut portion 56 screwed to the screw shaft 55 and slidable along a guide portion in the backand-forth direction, an oscillating piece 57 attached to the oscillation body 52, a connecting rod 58 in the back-and-forth direction of which rear end is attached to the nut portion 56 and front end is attached to the oscillating piece 57, plural sensors 60 which detect both of front and rear edges 59 of the belt 2 set around the pair of rotating drums 1a and 1b, and a control portion 61 electrically connected to each of the sensors 60 which rotates the motor 54 in one direction or the other according to detection signals from the sensors 60. Further, the oscillation body 52 and the short shaft 53 as composition members of the drum transfering mechanism 41 are shared with the meandering prevention mechanism 45.

As the sensor 60, for example, an infrared sensor is used. And, for example, two sensors 60 are disposed on the both edges 59 sides of the belt 2 respectively, and two emission portions 62 which emit infrared 63 to each of the sensors 60 are disposed on the both edges 59 sides of the belt 2 respectively.

That is to say, the front edge 59 or the rear edge 59 of the belt 2 rotated by the rotating drums 1 blocks the infrared 63 from the emission portion 62 on the front edge 59 side or the rear edge 59 side, a detection signal is output from the sensor 60 of which infrared 63 is blocked to the control portion 61, and the control portion 61 rotates the screw shaft 55 attached to the motor 54 in one direction or the other according to the detection signal. Therefore, the oscillating piece 57 and the oscillation body 52 are rotated around the vertical shaft 51, and the short shaft 53 and the driven rotating drum 1b is oscillated thereby. That is to say, the driven rotating drum 1b is slightly angled. In this case, the rotation drum 1b is rotated as to make distance L between the drums on the output sensor 60 side long. Then, the belt 2 is moved to the side of shorter distance L between the drums, and the motor 54 stops when the edge 59 of the belt 2 receiving the infrared 63 deviates from the infrared 63.

Next, as shown in FIG. 1 and FIGS. 7 through 9, the belt supporting means 5 has a flat stage 64 facing the inner face 4 of the endless belt 2 and a function that supplies water between the flat stage 64 and the belt 2 from an upstream side of belt-rotation direction (a direction shown with an arrow A) to the flat stage 64.

Figure 8:
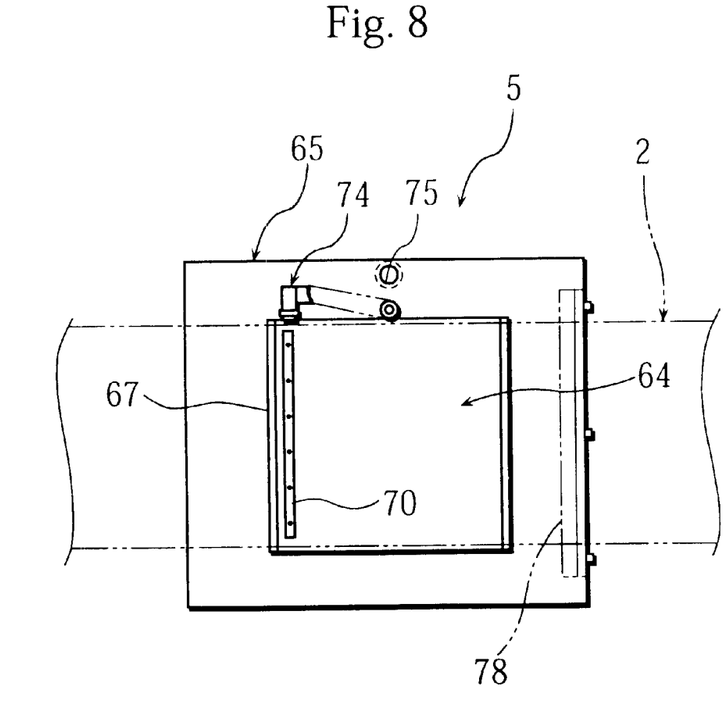
FIG. 8 is a top view of a principal portion showing a flat stage of the supporting means.

To describe concretely, the belt supporting means 5 is provided with a pan body 65 opening upward disposed between the pair of rotating drums 1, plural supporting posts 66 penetrate a bottom wall of the pan body 65 as to tightly close and support the pan body 65, the above-mentioned rectangular flat stage 64 attached to upper ends of the supporting posts 66 through an attachment member 67, and a water-supplying mechanism 68 which supplies water between the flat stage 64 and the inner face 4 on an upper side of the belt 2. The flat stage 64 is preferably formed with a low-friction member. And, lower ends of the supporting posts 66 are penetrating the rear wall of the constant temperature chamber 9 and fixed to the frame plate 43 as not to contact the inner face 4 on a lower side of the belt 2.

The water-supplying mechanism 68 is provided with a constant low temperature chamber 72 disposed in a base frame 69, a water-supplying pump 73 connected to the constant low temperature chamber 72, a row of waterjet groove 70 formed on an upper face 64a of the flat stage 64 on the upstream side of belt-rotation direction (the direction of the arrow A) in a direction at right angles with the belt-rotation direction, and a water-supplying pipe 74 penetrating the pan body 65 as to tightly close for connecting the water-supplying pump 73 and the waterjet groove 70. A drain hole 75 is formed on the bottom wall of the pan body 65 and a drain pipe 76 is connected to the drain hole 75 to drain or circulate the water dropped in the pan body 65 by returning to the constant low temperature chamber 72. And, a wiper 78 for wiping off water drops on the inner face 4 of the belt 2 is attached to an upper brim on the downstream side of the pan body 65.

Next, an example of friction test and working of the friction test apparatus are described with reference to FIG. 1 through FIG. 9. For example, in case that friction test of the sample W as a composition material of a tire is conducted, the sample W of ring is set on the sample holder 6. And, in the rotating friction means 3, tension of the belt 2 is adjusted to be a set value (100 kgf, for example) by moving the driven rotating drum 1b left and right in FIG. 1 with the drum transfering mechanism 41.

Figure 9:
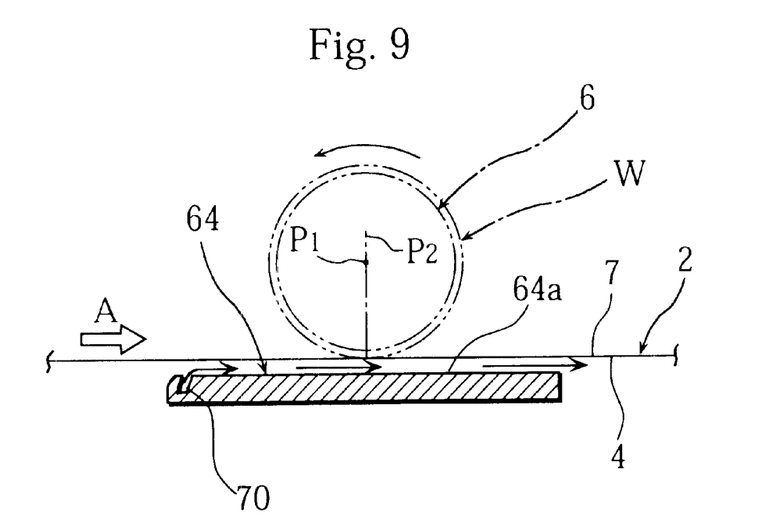
FIG. 9 is an explanatory view showing a state in which a water film is formed between a belt and the flat stage.

Then, the water in the constant low temperature chamber 72 is supplied to the waterjet groove 70 on the flat stage 64 by driving the water-supplying pump 73 of the belt supporting means 5, and the rotating friction means 3 rotates the driving rotating drum 1a to rotate the belt 2 at a set rotation frequency. In this case, the water blown out of the waterjet groove 70 is expanded in the rotation direction (the direction of the arrow A) by the rotation of the belt 2, and a water film is formed between the flat stage 64 and the belt 2 thereby.

And, the sample holder driving means 8 rotates the sample holder 6 to the set rotation frequency and descends the sample W attached to the sample holder 6 to the outer face (upper face) of the belt 2 or near the outer face 7 with driving the sample transfer cylinder 31 of the sample measuring portion 10. And, the sample W attached to the sample holder 6 is pressurized on the outer face 7 of the belt 2 with a set load by driving the sample loading cylinder 35. In this case, the load on the sample W is detected by the three-component detecting portion 34, the detected load is fed back to the load control portion, and the air pressure is automatically controlled by the air-pressure source unit of the cylinder 35 as to set the value of the fed-back load to be a predetermined pressure.

Next, in case that slip ratio test is conducted under the conditions above, torque working on a rotation shaft 6a of the sample holder 6 is detected by the torque detecting portion, and the rotation frequency of the sample W (the rotation frequency of the sample holder 6) is increased or decreased as to make the torque 0 when the torque works in the rotation direction. And, after the torque is adjusted to be 0, the sample W is decelerated until the slip ratio becomes a predetermined value, torque working on the rotation shaft 6a of the sample holder 6 is measured by the torque detecting portion when the slip ratio becomes the predetermined value, and the loads working on the sample in front-rear direction, left-right direction, and upper-lower direction are measured by the above-mentioned three-component detecting portion 34. That is to say, thrust load on the front and rear parts of the sample, load in the belt-rotation direction on the left and right parts of the sample, and press load on the upper and lower parts of the sample are detected by the three-component detecting portion 34.

And, in case that slip angle test is conducted, the belt 2 is rotated with the set rotation frequency (as described above), and the sample W is pressurized with the set load. In this case, the test may be conducted with rotation of the sample W. And, the load on the sample W is detected by the three-component detecting portion 34, the detected load is fed back to the load control portion, and the air pressure is automatically controlled by the air-pressure source unit as to set the value of the fed-back load to be a predetermined pressure. And, after the pressure on the sample W is adjusted to be the predetermined pressure, the sample W is angled to a predetermined slip angle θ (as shown in FIG. 3 and FIG. 6). That is to say, the sample W is angled with a predetermined slip angle θ to the belt 2 by oscillating the rotational axis $P_1$, of the sample holder 6 with the slip angle regulation mechanism 11. Then, torque on the rotation shaft 6a of the sample holder 6 is measured by the torque detecting portion, and the loads working on the sample W in front-rear direction, left-right direction, and upper-lower direction are measured by the three-component detecting portion 34.

Although accurate analysis can not be conducted only with the thrust load and the press load because "twisting" force by the slip angle works on the rotation shaft 6a of the sample holder 6 in the slip angle test, sufficiently accurate analysis can be conducted by the present invention because load in the running direction of the belt is also measured by the three-component detecting portion 34.

Further, in the slip ratio test and the slip angle test as described above, although the belt 2 is pushed by the sample W to the flat stage 64 side, the frictional force on the sample W can be accurately measured because the rotation frequency of the belt is not changed by contact of the belt 2 and the flat stage 64 which do not contact each other for the water film formed between the belt 2 and the flat stage 64, and meandering of the belt 2 in rotation is prevented by the meandering prevention mechanism 45 combined with the rotating friction means 3. And, although abrasion is barely generated in the friction test apparatus of the present invention that measures friction characteristics of the sample W, abrasion of small amount left on the belt 2 is removed by air blown out of the air blowing portion 77 disposed near the driven rotating drum 1*b*.

According to the friction test apparatus of the present invention, friction test is conducted with the sample W under the same conditions in friction test with products, labor and time for making prototype of the products are greatly saved, and production cost is also reduced. And, the endless belt 2 is rotated without meandering by the meandering prevention mechanism 45, the friction characteristics of the sample W can be measured with accuracy.

And, the belt 2 and the flat stage 64 do not contact when the sample W is pressed to the belt 2 in friction test because a water film is formed between the rotating endless belt 2 and the flat stage 64. Therefore, change in rotation frequency of the belt by contact of the belt and the stage is not caused, and frictional force on the sample W is measured accurately further. And, the construction of the water-supplying mechanism 68 can be simplified because the water is expanded by the rotating belt 2 to make the water film.

And, the thrust load working on the front and the rear parts of the sample W, the load in the belt-rotation direction on the left and right parts of the sample, and the press load on the upper and lower parts of the sample can be measured by the three-component detecting portion 34. Therefore, accurate data analysis can be conducted even in the case that the sample W is slip-angled.

Further, the apparatus of the present invention is preferable as a friction test apparatus to simulate actual running conditions with product tires because the slip angle test and the slip ratio test can be conducted.

While preferred embodiments of the present invention have been described in this specification, it is to be understood that the invention is illustrative and not restrictive, because various changes are possible within the spirit and indispensable features.

What is claimed is:

1. A friction test apparatus comprising a rotating friction means, having an endless belt set around one pair of rotating drums, a belt supporting means disposed near an inner face of the belt, a sample holder to which a sample is detachably attached, a sample holder driving means which holds the sample holder so as to rotate and by which the sample attached to the sample holder is pressed to and parted from an outer face of the belt, and a meandering prevention mechanism to prevent the belt rotated by the pair of rotating drums from meandering, wherein the belt supporting means has a flat stage facing the inner face of the belt and a water supplying mechanism which supplies water between the flat stage and the belt from an upstream side of belt rotation direction to the flat stage, wherein the sample holder driving means is having a slip angle regulation mechanism for regulation of a slip angle of the sample attached to the sample holder to the belt, and constructed so as to adjust the slip ratio of the sample attached to the sample holder to the belt.

2. The friction test apparatus as set forth in claim 1, wherein the sample holder driving means has a three-component detecting portion which detects loads on the sample in front-rear direction, left-right direction and upper-lower direction.

3. A friction test apparatus comprising a rotating friction means having an endless belt set around one pair of rotating drums, a belt supporting means disposed near an inner face of the belt, a sample holder to which a sample is detachably attached, a sample holder driving means which holds the sample holder so as to rotate and by which the sample attached to the sample holder is pressed to and parted from an outer face of the belt, and a meandering prevention mechanism to prevent the belt rotated by the pair of rotating drums from meandering, wherein the sample holder driving means is having a slip angle regulation mechanism for regulation of a slip angle of the sample attached to the sample holder to the belt, and constructed so as to adjust the slip ratio of the sample attached to the sample holder to the belt.

4. The friction test apparatus as set forth in claim 3, wherein the sample holder driving means has a three-component detecting portion that detects load on the sample in front-rear direction, left-right direction, and upper-lower direction.

* * * * *